United States Patent [19]

Tóth et al.

[11] Patent Number: 4,645,779
[45] Date of Patent: Feb. 24, 1987

[54] DIALKYLAMINOALKOXYBENZYLALCOHOL DERIVATIVES, PROCESS FOR THEIR PREPARATION AND PHARMACEUTICAL COMPOSITIONS CONTAINING THEM

[75] Inventors: Edit Tóth; József Törley; György Fekete; László Szporny; László Vereczkey; Éva Pálosi; Imre Klebovich; Pál Vittay; Sándor Görög; István Hajdu, all of Budapest, Hungary

[73] Assignee: Richter Gedeon Vegyeszeti Gyar Rt, Budapest, Hungary

[21] Appl. No.: 565,913

[22] Filed: Dec. 27, 1983

[30] Foreign Application Priority Data

Dec. 28, 1982 [HU] Hungary ............................. 4192/82

[51] Int. Cl.$^4$ ..................... C07C 87/30; C07C 149/32
[52] U.S. Cl. .................................. 514/648; 514/554;
260/501.15; 260/501.18; 564/283; 564/324
[58] Field of Search ................... 564/324; 260/501.18;
424/316, 330; 514/648, 554

[56] References Cited
U.S. PATENT DOCUMENTS 3,494,961 2/1970 Ruegg et al. ................... 564/324 X
4,094,908 6/1978 Toth et al. ........................... 564/324

*Primary Examiner*—Robert V. Hines
*Attorney, Agent, or Firm*—Karl F. Ross; Herbert Dubno

[57] ABSTRACT

The invention relates to new dialkylaminoalkoxybenzylalcohol derivatives of the formula (I)

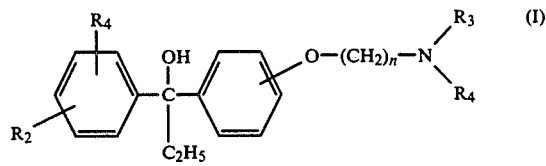

wherein
  $R_1$ is hydrogen, halogen, trihalomethyl, alkyl having from one to 4 carbon atoms or alkoxy having from one to 4 carbon atoms;
  $R_2$ is halogen, trihalomethyl, alkyl having from one to 4 carbon atoms or alkoxy having from one to 4 carbon atoms;
  $R_3$ and $R_4$ independently stand for an alkyl group having from 3 to 5 carbon atoms; and
  n is 2, 3, 4 or 5, and acid addition and quanernary ammonium salts thereof.

According to another aspect of the invention there are provided processes for the preparation of these compounds.

The new compounds provided by the invention are pharmaceutically active, in particular, they are suitable for the treatment of acute ethanolic intoxication. Pharmaceutical compositions containing them as active ingredient are another aspect of the invention.

4 Claims, No Drawings

DIALKYLAMINOALKOXYBENZYLALCOHOL DERIVATIVES, PROCESS FOR THEIR PREPARATION AND PHARMACEUTICAL COMPOSITIONS CONTAINING THEM

The invention relates to new dialkylaminoalkoxybenzylalcohol derivatives of the formula (I)

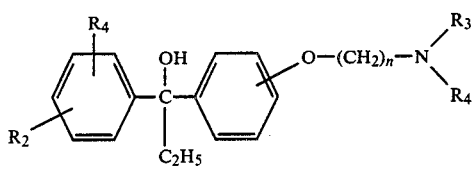

wherein
$R_1$ is hydrogen, halogen, trihalomethyl, alkyl having from one to 4 carbon atoms or alkoxy having from one to 4 carbon atoms;
$R_2$ is halogen, trihalomethyl, alkyl having from one to 4 carbon atoms or alkoxy having from one to 4 carbon atoms;
$R_3$ and $R_4$ independently stand for an alkyl group having from three to 5 carbon atoms; and
n is 2, 3, 4 or 5,
and acid addition and quaternary ammonium salts thereof. The compounds of the formula (I) are suitable for the treatment of acute ethanolic intoxication. Pharmaceutical compositions containing them as active ingredient are another aspect of the invention.

The term "halogen" as used herein embraces all of the halogens, and may be fluorine, chlorine, bromine or iodine, preferably fluorine or chlorine.

The term "alkyl" refers to straight or branched chained aliphatic hydrocarbon groups. If the alkyl groups contain from one to 4 carbon atoms, they include methyl, ethyl, n- or i-propyl, n-, sec- or tert-butyl. The alkyl groups containing from 3 to 5 carbon atoms may be n- and i-propyl, n-, sec- or tet-butyl, n- or i-pentyl groups.

The term "alkoxy having from one to 4 carbon atoms" is used herein to refer to straight or branched chained alkoxy groups containing from one to 4 carbon atoms, e.g. methoxy, ethoxy, n- and i-propoxy, n-, sec- or tert-butoxy, preferably methoxy.

The trihalomethyl groups may contain any of the halogens listed above, preferably fluorine.

Compounds of analogous structure are disclosed for example in the following references: C.A. 22, 410[1]; 35, 1781[2]; 40, 4712[5]; 42, P 1015 b; 47, 9548 e; 50, 12390 c; 50, 2509 i; 55, 17915 e; 55, 15413 b; 75, P 103682 b; 76, P 119921 k; 82, 16477 g; 90, 86082 g; 92, 52927 b. None of these citations, however, mentions any pharmaceutical activity of the disclosed compounds.

The new compounds of the formula (I) can be prepared by
(a) reacting a propiophenone of the formula (II)

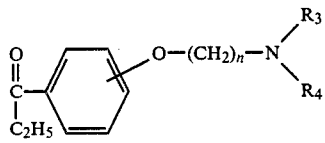

wherein $R_3$, $R_4$ and n each have the same meanings as defined above, with an organometallic compound of the formula (III)

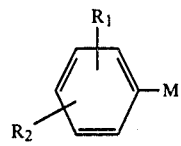

wherein
$R_1$ and $R_2$ are as defined above, and
M is an alkali metal, preferably lithium, sodium or potassium, or an MgX group, in which X is halogen; or
(b) reacting a compound of the formula (IV)

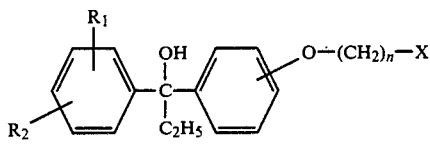

wherein $R_1$, $R_2$ and n each have the same meanings as defined above, and X is halogen, with an amine of the formula (V)

wherein $R_3$ and $R_4$ are as defined above, preferably in the presence of a base; or
(c) reacting a benzophenone of the formula (VI)

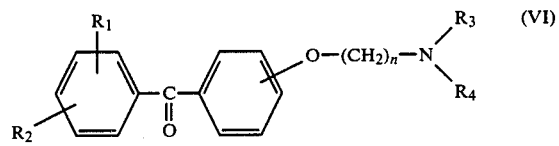

wherein $R_1$, $R_2$, $R_3$, $R_4$ and n each have the same meanings as defined above, with an organometallic compound containing an ethyl group, preferably an ethyl magnesium halide or ethyl lithium; or
(d) reacting a propiophenone of the formula (VII)

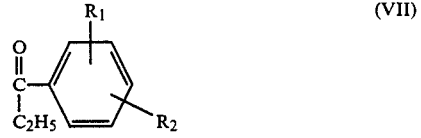

wherein $R_1$ and $R_2$ are as defined above, with a Grignard compound of the formula (VIII)

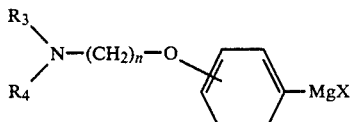

wherein R₃, R₄ and n each have the same meanings as defined above, and X is halogen; or (e) reacting a compound of the formula (IX)

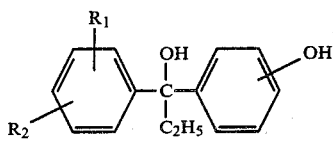 (IX)

wherein R₁ and R₂ are as defined above, preferably in the form of an alkali metal or quaternary ammonium phenolate thereof, with an amine of the formula (X)

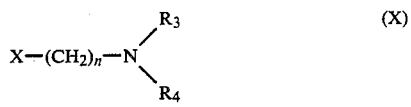 (X)

wherein R₃ and R₄ are as defined above, and X is halogen, alkylsulfonyloxy or arylsulfonyloxy group, or a salt thereof, preferably in the presence of an acid binding agent; or (f) reducing a compound of the formula (XI)

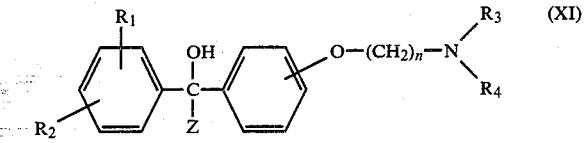 (XI)

wherein R₁, R₂, R₃, R₄ and n each have the same meanings as defined above, and Z is ethinyl or vinyl, and if desired, converting any of the products obtained by process variants (a) to (f) into their acid addition or quaternary ammonium salts, or converting a product obtained as an acid addition salt into a corresponding base and/or converting a free base into an acid addition or quaternary ammonium salt thereof.

According to a preferred embodiment of process variant (a) propiophenones of the formula (II) are reacted with the organometallic compounds of the formula (III), preferably with an appropriately substituted phenyl magnesium chloride or bromide or an appropriately substituted phenyl lithium, in an anhydrous inert organic solvent. The reaction is carried out preferably in an aprotic organic solvent, e.g. in an aliphatic ether such as diethyl ether, di-n-butyl ether or diethylene glycol dimethyl ether, an alicyclic ether such as tetrahydrofuran, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. in nitrogen or argon. The reaction temperature may range from −60° C. up to the boiling point of the solvent, and preferably is between −30° C. and 100° C. When the reaction is complete, the reaction mixture is decomposed, preferably with an aqueous ammonium chloride solution, and the obtained compound of the formula (I) is separated. The product can be purified by known techniques, e.g. by distillation or crystallization.

According to process variant (b) compounds of the formula (IV), in which X preferably represents chlorine or bromine, are reacted with a secondary amine of the formula (V). The reaction is preferably accomplished in an organic solvent, in the presence of a base suitable for binding the acid formed in the reaction. As a solvent for example hydrocarbons such as ligroin, benzene, toluene, halogenated hydrocarbons such as chloroform, ethers such as dioxane, alcohols such as ethanol, esters such as ethyl acetate, acid amides such as dimethyl formamide, ketones such as acetone or methyl isobutyl ketone, or a mixture of these solvents can be employed. As an acid binding agent preferably inorganic or tertiary organic bases or an excess of the amine of the formula (V) is employed. If the excess of the amine of formula (V) is a tertiary organic base is used to bind the hydrogen halide formed in the reaction, these may well serve as a solvent, too. The reaction is carried out at a temperature between 20° C. and the boiling point of the solvent. After termination of the reaction the product is isolated, e.g. by pouring the reaction mixture onto water, and separating the product by solvent extraction. The organic phase is washed to halogen-free with water, dried and evaporated. The crude product can be purified for instance by distillation or crystallization.

According to process variant (c) a benzophenone of the formula (VI) is preferably reacted with an at least equimolar amount of ethyl magnesium bromide or ethyl magnesium iodide or ethyl lithium. The reaction is accomplished in an inert, dry organic solvent, essentially as described in connection with process variant (a).

According to process variant (d) the Grignard compounds of the formula (VIII), in particular those in which X is bromine, are reacted with an at least equimolar amount of propiophenones of the formula (VII) in an anhydrous inert organic solvent, similarly to process variant (a).

According to a preferred embodiment of process variant (e) compounds of the formula (IX) in form of their alkali metal or quaternary ammonium phenolates, are condensed with the tertiary amines of the formula (X). As a tertiary amine e.g. dialkylaminoalkyl mesylates, tosylates, bromides or preferably chlorides are employed, as a free base or a salt, e.g. hydrogen halide thereof. The reaction is preferably carried out in an inert organic solvent, in the presence of an acid binding agent, under anhydrous conditions or in a mixture of water and an organic solvent. As organic solvents for example esters such as ethyl acetate, ethers such as dioxane, tetrahydrofuran or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (IX) can be converted into their phenolates by methods known in the art, e.g, with alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodide may be used. The reaction temperature may be varied within a wide range, and preferably is between 20° C. and the boiling point of the solvent.

According to a preferred embodiment of process variant (f) the ethinyl or vinyl compounds of the formula (XI) are reduced by catalytic hydrogenation. Suitable catalysts include metals such as ruthenium, palladium platinum, nickel, iron, copper, cobalt, chromium, zinc, molybdenum, tungsten, etc. and the oxides and sulfides of these metals. The catalysts may be prepared by reducing their stable oxides with hydrogen, directly in the reaction vessel. This procedure is especially suitable for the preparation of a finely dispersed platinum or palladium catalyst. Catalytic hydrogenation may be accomplished also in the presence of catalysts precipitated on the surface of a carrier, e.g. charcoal, silica, alumina or sulfates or carbonates of the alkali earth metals. The reaction may be carried out also in the presence of a Raney-nickel catalyst. The catalytic hydrogenation is preferably performed in the presence of palladium, in particular palladium-on-charcoal or Raney-nickel, in an organic solvent inert under the reaction conditions. As a solvent for example lower aliphatic alcohols, ethers, esters, aliphatic, cycloaliphatic and aromatic hydrocarbons or mixtures of these solvents may be employed. The hydrogenation may be carried out under atmospheric or higher pressure, preferably not exceeding 506 kPa, at a temperature between 20° C. and the boiling point of the solvent employed. The reduction is preferably carried out at room temperature, under atmospheric pressure until ceasing of the hydrogen uptake. The catalyst is then filtered off, the filtrate is evaporated, and if desired, the product is purified, e.g. by distillation or crystallization.

If desired, the compounds of the formula (I) can be converted into their acid addition salts or quaternary ammonium salts by methods well known in the art. The acid addition salts can be prepared by means of inorganic or organic acids, e.g. hydrogen halides such as hydrochloric acid, hydrogen bromide, etc., sulfuric acid, phosphoric acids, formic acid, acetic acid, propionic acid, oxalic acid, glycolic acid, maleic acid, fumaric acid, tartaric acid, succinic acid, ascorbic acid, citric acid, cinnamic acid, asparaginic acid, glutaminic acid, N-acetyl-asparaginic acid, N-acetyl-glutaminic acid, alkylsulfonic acids such as p-toluene-sulfonic acid, etc. According to a preferred embodiment the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture of these solvents, at a temperature between room temperature and the boiling point of the solvent. The quaternary salts can be isolated e.g. by filtration and, if desired, are purified by crystallization.

The starting materials are known in the art or can be prepared by well known methods. Ketones of the formulae (II), (VI) and (VII) can for example be prepared by the Friedel-Crafts type ketone synthesis (G. A. Olah: Friedel-Crafts and Related Reactions, III/1, Ed.: Interscience Publishers (1964), pp.1–63).

The Grignard compounds of the formulae (III) and (VIII) are for example prepared from the corresponding substituted aryl halides by known techniques (M. S. Kharash et al.: Grignard Reactions of Nonmetallic Substances, Ed., Prentice-Hall. Inc. (1954) 5–90), while the alkali metal-organic compounds can be prepared following the method disclosed in Houben-Weyl: Methoden der Organischen Chemie, XIII/1, pp. 134–159 and 389–405 (1970).

The compounds of the formulae (IV) and (IX) can for example be synthesized starting from the corresponding substituted propiophenones, by Grignard reactants, following techniques well known in the art (e.g. M. S. Kharash et al.: Grignard Reactions of Nonmetallic Substances, Ed.: Prentice-Hall Inc. (1954) pp. 138–143).

Compounds of the formula (XI), in which Z represents a vinyl group, are for example obtained by reacting a benzophenone of the formula (VI) with a vinyl magnesium halide, while compounds of the formula (XI), in which Z is an ethinyl group, are easily prepared by ethinylation of a benzophenone of the formula (VI), following the procedure described in the Hungarian Patent Specification No. 166,769.

The new compounds of the formula (I) and their salts possess valuable pharmacological properties. More particularly, these compounds are suitable for the treatment of acute ethanolic intoxication and can, therefore, widely be used in therapy. Acute alcoholic intoxication is characterized by euphoria, general stimulation, ataxia, somnolence, paralytic condition, etc. The dangers of this toxic, pathologic condition are well known and cannot be neglected. The intoxicated person is a threat to his environment (e.g. driving while intoxicated) and exposes his own health to danger. The acute alcoholic intoxication is an essential "risk factor" of cerebral ischaemic infarcts (Hillbom, M. et al.: Lancet, 2, 1181 (1978); Stroke, 12, 422 (1981)). The ethanolic intoxicated condition has no satisfactory antidote. Although α-methyl-paratyrosine normalizes the ethanolic locomotoric hyperactivity on mice, it is effective in a dose range in which a decrease of the spontaneous locomotoric activity of animals takes also place (Carlsson, A, et al: Psychopharm., 26, 307 (1972)). On the other hand, stimulants like caffeine and amphetamine moderate the narcotizing effect of alcohol, but also prolong the motoric incoordination (ataxia) (Wallagsen, H. et al.: Actions of alcohol, Amsterdam; Elsevier 1970; R. H. Rech et al.: Ann. N.Y. Acad. Sci., 28, 426 (1976); Todzy, I. et al.: Psychopharm., 59, 143 (1976)). The alcoholic intoxication, i.e. the narcosis period is shortened by L-cysteine (Sprince, H. et al.: Agents and Actions, 4, 125 (1974); Nagasawa, H. T. et al.: Life Sci., 17, 707 (1975)). This compound was used as a reference substance in our ethanolic narcosis period tests.

The effect of the compounds according to the invention on ethanolic narcosis period was tested on Hann.-Wistar rats of both sexes, weighing 160 to 180 g. each. The animals were fasted for 16 hours prior to treatment. Groups of ten were then treated with various doses of the compounds of the formula (I) orally. One hour after treatment the animals were given a 3.5 g./kg. dose of ethanol, intraperitoneally. The narcosis period of the animals was measured from the elapse of the righting reflex until a spontaneous correction of the body position. The average of the narcosis period and the standard error were calculated, and the results are given in percentage of the control in Table 1.

Abbreviations:
$\bar{x} \pm S.E.$ = means value ± standard error
n = number of animals The control group was treated with a placebo and a 3.5 mg./kg. dose of ethanol.

Narcosis period of the control:
88.5 ± 3.54 $\bar{x} \pm S.E.$ minutes
A = α-ethyl-α-(2-methoxyphenyl)-4-[3-(di-n-propylamino)-propoxy]-benzylalcohol B=α-ethyl-α-(3-chlorophenyl)-4-[3-(di-n-propylamino)-propoxy]-benzylalcohol
C=α-ethyl-α-(2-trifluoromethylphenyl)-4-[3-(di-isopropylamino)-ethoxy]-benzylalcohol

TABLE 1

| Compound | Dose (mg./kg.) | Ethanolic narcosis period control ± S.E. % | n |
|---|---|---|---|
| Control |  | 100 ± 4.0 | 10 |
| A | 5.0 | 60 ± 10.1 | 10 |
|  | 10.0 | 50 ± 6.9 | 10 |
| B | 0.3 | 65 ± 6.8 | 10 |
|  | 1.0 | 53 ± 4.7 | 10 |
|  | 10.0 | 49 ± 2.8 | 10 |
| C | 40.0 | 62 ± 5.1 | 10 |
| L-cysteine | 500.0 | 63 ± 4.2 | 10 |

As appears from the data set forth in Table 1, the compounds provided by the invention are potent antagonizers of the central nervous system depressing activity of ethanol and substantially shorten the ethanolic narcosis period. Their activity is the same or higher than the activity of L-cysteine when administered in 1-3 orders of magnitude smaller doses. Ethanol exerts a dose-dependent stimulating effect on the central nervous system and induces hyperactivity.

The effect of the compounds provided by the invention on ethanolic locomotoric hyperactivity was tested on BALB/c mice of both sexes, each weighing 16 to 18 g. The test materials were administered to groups of 15 in a 40 mg./kg. oral dose, one hour before administering a placebo orally or a 2 g./kg. dose of ethanol intraperitoneally. The control animals were treated with a placebo. The locomotor activity of the animals was measured for two hours, using an Animex BSE motimeter. The results are shown as a Table 2, in percentage of the control.

TABLE 2

| Compound | Dose (mg./kg.) Comp. | Dose (mg./kg.) Ethanol | Locomotor activity total motion/ 2 hour (%) | n |
|---|---|---|---|---|
| Control° | — | — | 100 ± 9.8 | 15 |
| Ethanol + placebo |  | 2000.0 | 170 ± 11.8 | 15 |
| B + placebo | 40 |  | 108 ± 13.3 | 15 |
| B + Ethanol | 40 | 2000.0 | 70 ± 8.4 | 15 |

°Control (treated with placebo): x̄ ± S.E. = 3118.3 ± 305.6 total motion/2 hours The compounds according to the invention substantially reduce the ethanol-induced increased locomotor activity, at the same time have no effect on the spontaneous locomotor activity of untreated animals.

The acute toxicity of the compounds provided by the invention was determined on Wistar rats of both sexes, each weighing 160 to 180 g., which had been treated with a single 500 mg./kg. dose of the test compounds, orally. The animals were observed for 14 days after treatment. In Table 3 the percentage of the perished animals is given.

TABLE 3

| Compound (500 mg./kg. p.o.) | Perished animals (%) | n |
|---|---|---|
| A | 0 | 10 |
| B | 0 | 10 |
| C | 0 | 10 |
| L-cysteine | 0 | 10 |

The toxicity of the compounds according to the invention is favorably low related to the effective dose.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol, Exp. Ther. 132, 360 (1961)), nicotine spasm (Stone, C. A., Mecklenburg, K. L., Torhans, M. L.: Arch. Int. Pharmacodyn. 117, 419 (1958)), rotarod test (Kinnard, W. C., Carr, C. J.: J. Pharmacol. Expt. Ther. 121, 354 (1957)), physostigmine lethality preventing effect (Nose, T., Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, G., Francheschini, J.: Brit. J. Pharm. Chemother. 9, 280 (1954)). When administered in a 160 mg./kg. dose, the compounds according to the invention showed no CNS-activity in the above tests.

The results show that the compounds provided by the invention have a favorable influence on the behavior forms altered by ethanol. They antagonize both the CNS-stimulating and the CNS-depressing effect of alcohol, shorten the time in which the intoxicated person becomes intact again, have a favorable toxicity and a great therapeutic range.

The pharmacologically active compounds according to the invention can be used in therapy in the form of pharmaceutical compositions, which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose, polyvinyl pyrrolidone or starch gum, as a disintegrating substance e.g. potato starch or microcrystalline cellulose, ultraamylopectin or formaldehyde casein, etc. The formulations may also contain antiadhesives and lubricants such as talc, colloidal silica, stearin, calcium or magnesium stearate, etc.

Tablets are prepared for example by wet granulation and subsequent pressing. A mixture of the active ingredient and the vehicle and optionally a portion of the disintegrating agent are granulated with an aqueous, alcoholic or aqueous-alcoholic solution of the excipients in a suitable apparatus, and the granulate is dried. The remaining portions of the disintegrating substance, lubricant, antiadhesive or optional further additives are then added to the granules, and the mixture is pressed to tablets. If desired, the tablets are prepared with a dividing line which facilitates administration. Tablets can be prepared also from a mixture of the active ingredient and suitable additives by direct pressing.

If desired, the tablets can be converted to dragées, using protecting, flavoring agents and pigments generally known for the preparation of pharmaceutical compositions, e.g. sugar, cellulose derivatives (methyl or ethyl cellulose, carboxymethyl cellulose sodium etc.), polyvinylpyrrolidone, calcium phosphate, calcium carbonate, food pigment, food oil varnishes, aroma substances, iron oxide pigments, etc.

Capsules are prepared by filling a mixture of the active ingredient and the additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogenously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind the metal traces such as ethylene diamine tetraacetate, buffers to adjust the pH and optionally local anaesthetics such as lidocaine. The injectable solutions are filtered, filled into ampoules and sterilized.

The daily dose, depending on the patient's condition, varies between 0.1 and 300.0 mg./kg., preferably 2.0 and 160 mg./kg., preferably administered in a number of smaller portions.

The invention will be further described with reference to the following illustrative Examples.

EXAMPLE 1

α-Ethyl-α-(2-methoxyphenyl)-4-[2-(diisopropylamino)-ethoxy]-benzylalcohol

To a Grignard reactant prepared from 1.82 g. of magnesium turnings and 14 g. of 2-bromo-anisole in 53 ml. of tetrahydrofuran a solution of 14 g. of 4-[2-(diisopropylamino)-ethoxy]-propiophenone in 30 ml. of tetrahydrofuran is added dropwise, with stirring under slight reflux. The reaction mixture is boiled for additional hour. It is cooled to room temperature and poured onto a saturated aqueous ammonium chloride solution. Tetrahydrofuran is distilled off under reduced pressure, and the residue is extracted with benzene. The benzene solution is washed with a saturated aqueous sodium chloride solution and subsequently with water, dried over anhydrous magnesium sulfate, filtered and evaporated in vacuo. Crystallization of the residue from n-hexane yields 15 g. of the named compound, which melts at 46° to 47° C.

Analysis for $C_{24}H_{35}NO_3$: Calculated: C 74.78%, H 9.15%, N 3.63%; Found: C 74.87%, H 9.23%, N 3.77%.

EXAMPLE 2

α-Ethyl-α-(4-fluorophenyl)-4-[3-(di-n-propylamino)-propoxy]-benzylalcohol

To an ethyl magnesium bromide solution prepared from 3.6 g. of magnesium turnings and 16.3 g. of ethyl bromide in 60 ml. of dry ether a solution of 13.2 g. of 4-fluoro-4'-[3-(dipropylamino)-propoxy]-benzophenone in 70 ml. of dry ether is added dropwise, with stirring at 0° to 5° C. The reaction mixture is stirred at room temperature for 30 minutes, and is then poured onto a solution of ammonium chloride in ice water. The aqueous phase is extracted with ether, the solvent phases are combined, washed to neutral with water and dried over anhydrous magnesium sulfate. Ether is distilled off under reduced pressure, and the residue is distilled off in vacuo. 11.7 g. of the named compound are obtained, boiling at 196° to 198° C./13 Pa.

Analysis for $C_{24}H_{34}FNO_2$: Calculated: C 74.38%, H 8.84%, F 4.90%, N 3.61%; Found: C 74.48%, H 3.87%, F 5.11%, N 3.72%.

By treating the base in a dry ethanolic solution with an ethanolic solution of an equimolar amount of fumaric acid and adding ether to the solution cooled to −10° C. the corresponding hydrogen fumarate is precipitated. The hydrogen fumarate salt is filtered off, washed with ether and dried. Melting point: 87° to 89° C.

EXAMPLE 3

α-Ethyl-α-(4-chlorophenyl)-4-[3-(di-n-propylamino)-propoxy]-benzylalcohol 13.1 g. of α-ethyl-α-(4-chlorophenyl)-4-hydroxy-benzylalcohol, 14 g. of anhydrous potassium carbonate, 9.8 g. of dipropylaminopropyl chloride and 0.85 g. of tetrabutyl ammonium hydrogensulfate in 135 ml. of ethyl acetate are slightly boiled for 20 hours, under stirring. After cooling the mixture, the solvent is evaporated in vacuo. To the residue water and benzene are added. The phases are separated, the benzene solution is washed with water, dried over anhydrous potassium carbonate, filtered and evaporated. The residue is purified by vacuum fractionation. 13.8 g. of the desired end product are obtained, boiling at 198° to 200° C./1.33 Pa.

Analysis for $C_{24}H_{34}ClNO_2$: Calculated: C 71.35%, H 8.48%, Cl 8.78%, N 3.47%; Found: C 71.41%, H 8.53%, Cl 8.94%, N 3.59%.

EXAMPLE 4

α-Ethyl-α-(2,4-dichlorophenyl)-4-[3-(dipropylamino)-propoxy]-benzylalcohol 21.7 g. of α-ethinyl-α-(2,4-dichlorophenyl)-4-[3-(dipropylamino)-propoxy]-benzylalcohol are dissolved in 210 ml. of benzene, and the solution is hydrogenated in the presence of 1.1 g. of a 10% palladium-on-charcoal catalyst. When the uptake of the calculated amount of hydrogen is complete (about 3 hours), catalyst is filtered off and benzene is distilled off. The crude product weighing 21 g. is distilled in vacuo, to yield a product boiling at 194° to 196° C./6.6 Pa.

Analysis for $C_{24}H_{29}Cl_2NO_2$: Calculated: C 65.74%, H 7.59%, Cl 16.17%, N 3.19%; Found: C 65.83%, H 7.74%, Cl 16.40%, N 3.15%.

α-Ethyl-α-(2,4-dichlorophenyl)-4-[3-(dipropylamino)-propoxy]-benzylalcohol methoiodide 4.4 g. of the above base and 12.4 g. of methyl iodide are dissolved in 22 ml. of acetone, and the reaction mixture is slightly refluxed for two hours, whereupon it is cooled to room temperature. The crystals precipitated upon addition of ether are filtered off and dried. 3.6 g. of the above quaternary compound are obtained, melting at 136° to 137° C.

EXAMPLE 5

α-Ethyl-α-(4-bromophenyl)-4-[3-(di-n-propylamino)-propoxy]-benzylalcohol

To a Grignard reactant prepared from 2.2 g. of magnesium turnings and 28.2 g. of 4-[3-(di-n-propylamino)-propoxy]-bromobenzene in 170 ml. of dry tetrahydrofuran a solution of 12.8 g. of 4-bromopropiophenone in 60 ml. of tetrahydrofuran is added dropwise, at 20° C., and the mixture is stirred at room temperature for two additional hours. When the reaction is complete, the reaction mixture is decomposed with a 20% aqueous ammonium chloride solution, under cooling. Tetrahydrofuran is distilled off under reduced pressure. The residue is extracted with benzene. The benzene phase is washed to neutral with water, dried over anhydrous magnesium sulfate, filtered and evaporated under reduced pressure. The residue is fractionated in vacuo. 19.9 g. of the desired end product are obtained, boiling at 220° to 224° C./6.6 Pa.

Analysis for $C_{24}H_{34}BrNO_2$: Calculated: C 64.28%, H 7.64%, Br 17.82%, N 3.12%; Found: C 64.40%, H 7.75%, Br 17.94%, N 3.28%.

The corresponding hydrogen fumarate melts at 106° C. to 107° C.

EXAMPLE 6

α-Ethyl-α-(3-chlorophenyl)-4-[3-(di-n-propylamino)-propoxy]-benzylalcohol 13.1 g of α-ethyl-α-(3-chlorophenyl)-4-hydroxy-benzylalcohol, 22.8 g. of anhydrous potassium carbonate and 0.4 ml. of a 40% tetrabutyl ammonium hydroxide solution in 130 ml. of methyl isobutyl ketone are brought to a boil, and a solution of 11.8 g. of di-n-propylaminopropyl chloride hydrochloride in 12 ml. of water is added, whereupon the reaction mixture is boiled for another 5 hours. The solvent is then distilled off under reduced pressure, to the residue water is added, and it is extracted with benzene. The benzene phases are combined, washed to neutral with a 5% aqueous potassium hydroxide solution and then with water, and dried over anhydrous magnesium sulfate. The solvent is distilled off under reduced pressure, the residue is fractionated. 13.5 g. of the desired compound are obtained, boiling at 200° to 202° C./6.6 Pa.

Analysis for $C_{24}H_{34}ClNO_2$: Calculated: C 71.35%, H 8.48%, Cl 8.78%, N 3.47%; Found: C 71.48%, H 9.55%, Cl 8.88%, N 3.52%.

Melting point of the corresponding hydrogen fumarate: 136° to 137° C.

EXAMPLE 7

α-Ethyl-α-(3-trifluoromethylphenyl)-4-[3-(di-n-propylamino)-propoxy]-benzylalcohol 20.8 g. of α-ethyl-α-(3-trifluoromethylphenyl)-4-(3-bromopropoxy)-benzylalcohol and 41 ml. of dipropyl amine are slightly refluxed with stirring for 6 hours. After cooling, the reaction mixture is evaporated under reduced pressure. To the residue water is added and it is extracted with benzene. The benzene phase is washed with water, dried over anhydrous potassium carbonate and evaporated. The residue is fractionated in vacuo to yield 17.2 g. of the desired compound, boiling at 176° to 178° C./6.6 Pa.

Analysis for $C_{25}H_{34}F_3NO_2$: Calculated: C 68.62%, H 7.83%, F 13.03%, N 3.20%; Found: C 68.57%, H 7.88%, F 13.17%, N 3.41%.

Melting point of the corresponding hydrogen fumarate: 85° to 86° C.

The following compounds can be prepared on the analogy of the above Examples, by proper selection of the starting substances.

α-Ethyl-α-(3-trifluoromethylphenyl)-4-[2-(diisopropylamino)-ethoxy]-benzylalcohol, boiling point: 172° to 174° C./6.6 Pa Analysis for $C_{24}H_{32}F_3NO_2$: Calculated: C 68.08%, H 7.62%, F 13.46%, N 3.31%; Found: C 68.22%, H 7.38%, F 13.70%, N 3.54%.

α-Ethyl-α-(4-chlorophenyl)-4-[2-(diisopropylamino)-ethoxy]-benzylalcohol, boiling point: 204° to 206° C./6.6 Pa Analysis for $C_{23}H_{32}Cl_2NO_2$: Calculated: C 70.84%, H 8.27%, Cl 9.09%, N 3.59%; Found: C 70.81%, H 8.18%, Cl 9.28%, N 3.77%.

α-Ethyl-α-(2-trifluoromethylphenyl)-4-[2-(diisopropylamino)-ethoxy]-benzylalcohol, boiling point: 197° to 201° C./20 Pa Analysis for $C_{24}H_{32}F_3NO_2$:

Calculated: C 68.06%, H 7.62%, F 13.56%, N 3.31%; Found: C 67.88%, H 7.73%, F 13.50%, N 3.10%.

α-Ethyl-α-(2-methoxyphenyl)-2-[2-(diisopropylamino)-ethoxy]-benzylalcohol, melting point: 71° to 72° C.

Analysis for $C_{24}H_{35}NO_3$: Calculated: C 74.78%, H 9.15%, N 3.63%; Found: C 74.70%, H 9.17%, N 3.84%.

α-Ethyl-α-(4-fluorophenyl)-4-[2-(diisopropylamino)-ethoxy]-benzylalcohol, boiling point: 191° to 194° C./13.3 Pa Analysis for $C_{23}H_{32}FNO_2$: Calculated: C 73.98%, H 8.64%, F 5.09%, N 3.75%; Found: C 74.23%, H 9.80%, F 5.34%, N 3.67%.

α-Ethyl-α-(2,5-dimethylphenyl)-4-[2-(diisopropylamino)-ethoxy]-benzylalcohol, boiling point: 200° to 204° C./13.3 Pa Analysis for $C_{25}H_{37}NO_2$:

Calculated: C 78.28%, H 9.72%, N 3.65%; Found: C 78.53%, H 10.01%, N 3.55%.

α-Ethyl-α-(3-chlorophenyl)-4-[2-(diisopropylamino)-ethoxy]-benzylalcohol.

boiling point: 190° to 192° C./6.6 Pa

Analysis for $C_{23}H_{32}ClNO_2$: Calculated: C 70.84%, H 8.27%, Cl 9.09%, N 3.59%; Found: C 71.10%, H 8.52%, Cl 9.17%, N 3.44%.

α-Ethyl-α-(2-methoxyphenyl)-4-[3-(di-n-propylamino)-propoxy]-benzylalcohol, boiling point: 212° to 214° C./6.6 Pa Analysis for $C_{25}H_{37}NO_3$: Calculated: C 75.15%, H 9.33%, N 3.50%; Found: C 75.23%, H 9.28%, N 3.63%.

Melting point of the corresponding hydrogen fumarate: 107° to 108° C.

EXAMPLE 8

The new compounds according to the invention can be converted for example into the following pharmaceutical compositions.

Tablets

Composition of a single tablet:

| | |
|---|---|
| active ingredient | 100.0 mg. |
| lactose | 184.0 mg. |

| | |
|---|---|
| potato starch | 80.0 mg. |
| polyvinyl pyrrolidone | 8.0 mg. |
| talc | 12.0 mg. |
| magnesium stearate | 2.0 mg. |
| aerosil (colloidal silica) | 2.0 mg. |
| ultraamylopectine | 12.0 mg. |

From the above ingredients 400-mg. tablets are prepared by wet granulation and subsequent pressing.

Active ingredient: α-ethyl-α-(2-methoxyphenyl)-4-[3-(di-n-propylamino)-propoxy]-benzylalcohol

Dragées

Tablets as described above are coated with a layer prepared from sugar and talc in a known manner. Dragées are polished with a mixture of bee wax and carnauba wax. Weight of a dragée: 500.0 mg.

Suppositories

Composition of a suppository:

| | |
|---|---|
| active ingredient | 100.0 mg. |
| lactose | 200.0 mg. |
| basic substance (e.g. Witepsol H) | 1700.0 mg. |

The basic substance is melted and then cooled to 35° C. The active ingredient is thoroughly admixed with the lactose, and the mixture is homogenized in the basic substance in a suitable equipment. The obtained mass is poured into cool mold. One suppository weights 2000 mg.

Active ingredient: α-ethyl-α-(3-chlorophenyl)-4-[3-(di-n-propylamino)-propoxy]-benzylalcohol.

Capsules

Composition of a capsule:

| | |
|---|---|
| active ingredient | 50.0 mg. |
| lactose | 100.0 mg. |
| talc | 2.0 mg. |
| potato starch | 30.0 mg. |
| cellulose (microcrystalline) | 8.0 mg. |

The active ingredient and the additives are thoroughly blended, the mixture is passed through a 0.32-mm. sieve and filled into hard gelatine capsules (size 4).

Active ingredient: α-ethyl-α-(3-chlorophenyl)-4-[3-(di-n-propylamino)-propoxy]-benzylalcohol

Suspensions

Composition of 100 ml. of suspension:

| | |
|---|---|
| active ingredient | 1.0 g. |
| sodium hydroxide | 0.26 g. |
| citric acid | 0.30 g. |
| nipagin (4-hydroxybenzoic acid methylester sodium salt) | 0.10 g. |
| Carbopol 940 (polyacrylic acid) | 0.30 g. |
| ethanol (96%) | 1.00 g. |
| raspberry aroma | 0.60 g. |
| sorbitol (70% aqueous solution) | 71.00 g. |
| distilled water ad | 100.0 ml. |

To a solution of nipagin and citric acid in 20 ml. of distilled water Carbopol is added in small portions, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbitol and an ethanolic raspberry aroma solution, with stirring. Active ingredient is added in small portions, and the mixture is homogenized. The suspension is supplemented with distilled water ad 100 ml., and the suspension syrup is passed through a colloid mill.

Active ingredient: α-ethyl-α-(2-trifluoromethylphenyl)-4-[3-(diisopropylamino)-ethoxy]-benzylalcohol.

We claim:

1. A compound of the Formula (I)

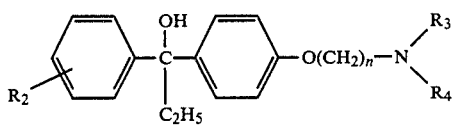

wherein

R$_2$ is halogen, trihalomethyl, or C$_1$ to C$_4$ alkoxy;

R$_3$ and R$_4$ independently stand for n-propyl or isopropyl; and n is 2 or 3; or a pharmaceutically acceptable acid addition or quaternary ammonium salt thereof.

2. The compound defined in claim 1 which is:
(a) alpha-ethyl-alpha-(3-chlorophenyl)-4-[3-(di-n-propyl-amino)-propoxy]-benzyl alcohol;
(b) alpha-ethyl-alpha-(2-trifluoromethylphenyl)-4-[2-(diisopropylamino)-ethoxy]-benzyl alcohol; or
(c) alpha-ethyl-alpha-(3-chlorophenyl)-4-[2-(diisopropylamino)-ethoxy]-benzyl alcohol; or a pharmaceutically acceptable acid addition or quaternary ammonium salt thereof.

3. A pharmaceutical composition for the treatment of ethanolic intoxication which comprises a pharmaceutically effective amount of the compound of the Formula (I) as defined in claim 1, or a pharmaceutically acceptable acid addition or quaternary ammonium salt thereof, in combination with a pharmaceutically acceptable inert carrier.

4. A method of treating ethanolic intoxication in an affected subject which comprises administering a pharmaceutically effective amount of the compound of the Formula (I) as defined in claim 1, or a pharmaceutically acceptable acid addition or quaternary ammonium salt thereof to said subject.

* * * * *